United States Patent
Winsness et al.

(10) Patent No.: US 10,435,657 B2
(45) Date of Patent: Oct. 8, 2019

(54) METHOD FOR PROCESSING BIOBASED MATERIALS AND THE RESULTING COMPOSITIONS

(71) Applicant: GENAREX FD LLC, Alpharetta, GA (US)

(72) Inventors: David James Winsness, Milton, GA (US); Jeffrey Jacob Cernohous, Hudson, WI (US); Robert William Montgomery, III, Lowell, MA (US)

( * ) Notice: Subject to any disclaimer, the term of this patent is extended or adjusted under 35 U.S.C. 154(b) by 169 days.

(21) Appl. No.: 15/515,025

(22) PCT Filed: Sep. 30, 2015

(86) PCT No.: PCT/US2015/053079
§ 371 (c)(1),
(2) Date: Mar. 28, 2017

(87) PCT Pub. No.: WO2016/054132
PCT Pub. Date: Apr. 7, 2016

(65) Prior Publication Data
US 2017/0218317 A1    Aug. 3, 2017

Related U.S. Application Data

(60) Provisional application No. 62/057,641, filed on Sep. 30, 2014.

(51) Int. Cl.
| | | |
|---|---|---|
| *C12F 3/10* | (2006.01) | |
| *C12P 7/08* | (2006.01) | |
| *C08K 11/00* | (2006.01) | |
| *C08H 8/00* | (2010.01) | |
| *C12P 7/06* | (2006.01) | |
| *C08L 89/04* | (2006.01) | |

(52) U.S. Cl.
CPC .............. *C12F 3/10* (2013.01); *C08H 8/00* (2013.01); *C08K 11/005* (2013.01); *C12P 7/08* (2013.01); *C08L 89/04* (2013.01); *C12P 7/06* (2013.01)

(58) Field of Classification Search
CPC ...... C12F 3/10; C12P 7/08; C12P 7/06; C08K 11/006; C08H 8/00; C08L 89/04
USPC ............................................. 524/560
See application file for complete search history.

(56) References Cited

U.S. PATENT DOCUMENTS

| | | | | |
|---|---|---|---|---|
| 8,809,425 B2 * | 8/2014 | Riebel | ........... | C12F 3/10 521/79 |
| 9,139,627 B2 * | 9/2015 | Riebel | ........... | C08H 1/00 |

FOREIGN PATENT DOCUMENTS

| | | |
|---|---|---|
| WO | 2013123400 A1 | 8/2013 |
| WO | 2016054132 A1 | 4/2016 |

OTHER PUBLICATIONS

Fallahi, Parisa et al. "Effects of Steam, Moisture, and Screw Speed on Physical Properties of DDGS-Based Extrudates", Cereal Chemisty, 2013, vol. 90, No. 3, pp. 186-197.
International Search Report issued in International Application No. PCT/US2015/053079, dated Jan. 21, 2016; 3 pages.
Kannadhason, S. et al., "Twin Screw Extrusion of DDGS-Based Aquaculture Feeds", Journal of the World Aquaculture Society, 2010, vol. 41, No. s1, Internal pp. 1-15.
Wang, L et al., "Thermal Degradation Kinetics of Distillers Grains and Solubles in Nitrogen and Air", Energy Sources, Part A, 2009, vol. 31, No. 10, pp. 797-806.
Written Opinion of the International Searching Authority, issued in International Application No. PCT/US2015/053079, dated Jan. 21, 2016; 6 pages.

* cited by examiner

*Primary Examiner* — Michael Bernshteyn
(74) *Attorney, Agent, or Firm* — Porzio Bromberg & Newman P.C.

(57) ABSTRACT

A method of treating a biobased feedstock derived from agricultural resources and specifically from the non-distillate products of fermentation-derived renewable fuel and distilled spirit processes. The separation of thermally labile components from biobased feedstocks result in materials that are thermally stable and better suited for subsequent melt processing in a polymer matrix.

36 Claims, 1 Drawing Sheet

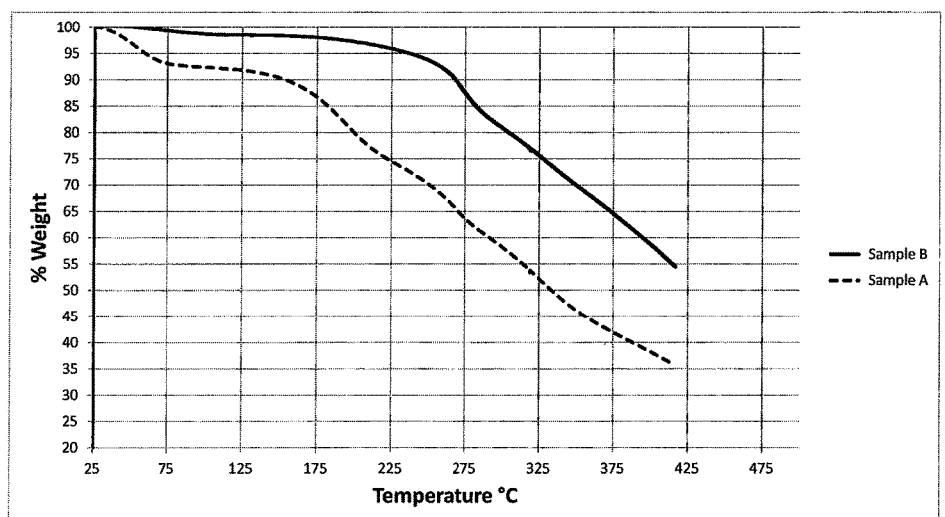

METHOD FOR PROCESSING BIOBASED MATERIALS AND THE RESULTING COMPOSITIONS

CROSS REFERENCE TO RELATED APPLICATIONS

This Application is a U.S. National Stage of International Application Number PCT/US2015/053079, filed Sep. 30, 2015, which claims the benefit of U.S. Provisional Application No. 62/057,641, filed Sep. 30, 2014, the entire disclosure of which is hereby incorporated by reference herein in its entirety.

BACKGROUND

This disclosure is directed to a method for treating a biobased feedstock generated as a co-product in fermentation-derived renewable fuel and distilled spirit production processes that utilize grain-based crops. The processing of the biobased feedstock by solvent extraction results in a composition that is well suited for subsequent melt processing with a polymer matrix.

The production of fermentation-derived renewable fuels or distilled spirits from grain-based agricultural materials often creates co-products that are generally sold as feed or burned or gasified for use as an energy source. The co-products are characterized as biobased feedstocks that result from the fermentation of grains. There have been various attempts to recover and refine such biobased feedstocks for uses that generate a greater value for the feedstock on a per pound basis. For example, distillers dried grains with solubles ("DDGS") have been placed in various plastics as fillers. However, such applications can be problematic with respect to achieving acceptable physical characteristics in the resulting composite materials.

One particular biobased feedstock is derived by distilling fermented grain-based material to produce a distillate fraction (such as ethanol or butanol) and a bottoms fraction, which is often referred to as whole stillage. The whole stillage is comprised of water and all of the parts of the fermented grain-based material that were not recovered in the distillate fraction. For corn-based ethanol processes, the whole stillage may comprise non-fermented starch and other carbohydrates, hemicellulose, corn hull, corn protein, corn fiber, corn oil, and ash. The whole stillage is typically subjected to a press or centrifugation process to separate the coarse solids from the liquid. The liquid fraction is commonly referred to as distillers solubles or thin stillage. Thin stillage is frequently concentrated in an evaporator to become condensed distillers solubles, often referred to as "CDS", which is also commonly referred to as syrup. The coarse solids, or wet cake, collected from the centrifuge or press are known as wet distillers grains. Drying the wet distillers grains produces dried distillers grains or "DDG." The wet distillers grains can be combined with the CDS to form what is commonly referred to as wet distillers grains with solubles, which can then be dried to form DDGS compounds. The industry continues to seek opportunities to place such materials in higher value products and applications.

SUMMARY

This disclosure is directed at treating a biobased feedstock derived from agricultural grains and specifically from the co-products of fermentation-derived renewable fuel or distilled spirit processes. More particularly, the separation of thermally labile components from biobased feedstocks by solvent extraction results in materials that are thermally stable and better suited for subsequent melt processing in a polymer matrix.

The biobased feedstock is generally the thin stillage resulting from fermentation-derived renewable fuel (such as ethanol or butanol) and distilled spirit production facilities that utilize grain-based crops. This thin stillage, upon additional evaporative processing that can include drying, may yield a biobased feedstock in concentrated fluid, powder or granular form that is further processed in accordance with this disclosure. In certain embodiments, the biobased feedstock is extruded to form an extrudate. The extrudate is then subjected to separation practices wherein at least a portion of thermally labile components are separated from the extrudate by solvent extraction. The resulting treated biobased feedstock is thermally stable at temperatures typically employed in the melt processing of polymers and composite materials, including polymers which are processed at temperatures above the decomposition temperature of biobased additives. In other embodiments, the extractant may be treated to recover nutrients or components of that particular stream.

In some embodiments, the treated biobased feedstock may be combined with a polymer matrix and other optional additives or adjuvants during melt processing to create a composite. The thermal stability of the treated biobased feedstock enables such melt processing without adverse consequence to the melt or the finished article. Additionally, in certain embodiments, the resulting composite may have enhanced physical properties such as tensile strength, flexural modulus, impact strength or combinations thereof.

The following terms used in this disclosure are defined as follows:

"Biobased feedstock" means the non-distillate products derived from the fermentation of grains, such as distillers solubles, for example.

"Composite" means a mixture of a polymer material and a biobased feedstock or treated biobased feedstock along with other optional additives and adjuvants.

"Degradation onset temperature" means the temperature at which a material (in this case the biobased component of a composite) begins to break down and decompose. This temperature may be represented by the point of inflection triggering mass loss in thermogravimetric analysis (TGA).

"Melt Processable Composition" means a formulation that is melt processed, typically at elevated temperatures, by means of a conventional polymer processing technique such as extrusion or injection molding as examples.

"Melt Processing Techniques" means extrusion, injection molding, blow molding, thermoforming, compression molding, or rotomolding batch mixing.

"Polymer Matrix" means a melt processable polymeric material or resin, e.g., a thermoplastic.

"Pyrolytic Modification" means the rapid heating of the biobased feedstock for the intentional removal of thermally labile components.

"Separation" or "Separating" means a process for converting a mixture of materials or compounds from a mixed state to a distinct and isolated state.

"Solvent Extraction" means separation of materials of different chemical types and solubilities by selective solvent action.

"Thermally labile" means components, such as inorganic compounds, organic compounds or polymers that decompose and/or outgas at temperatures below conventional polymer melt processing temperatures, for example, at temperatures below 250° C.

"Thermally stable" means a material's ability to withstand conventional melt processing temperatures without a significant loss of mass due to thermal degradation.

The disclosure may be understood more readily by reference to the following drawings and the detailed description of the various features described therein.

DESCRIPTION OF THE DRAWING

FIG. 1 is a chart of a thermogravimetric analysis indicating the degradation onset temperature of this disclosure.

DETAILED DESCRIPTION

This disclosure is directed to a method comprising extruding a biobased feedstock to form an extrudate and separating at least a portion of a thermally labile component from the extrudate to form a treated biobased feedstock. Due to the removal of the thermally labile components and a concomitant increase in thermal stability, the resulting treated biobased feedstock is well suited for subsequent use in melt processing applications with a polymer matrix. Because the treated biobased feedstock originates from a renewable source and is relatively inexpensive, the resulting article can be less expensive than traditional synthetic polymers. In general, it has been discovered that biobased feedstocks that have not been treated in this manner may contain thermally labile components. During melt processing applications, the biobased feedstocks having thermally labile components can adversely affect the integrity and physical characteristics of the resulting composite partly due to the decomposition or release of the thermally labile components. For example, extrusion of current biobased feedstocks with a polymeric matrix can result in weak materials or aesthetic properties that may not be desirable in some applications. The inventors have discovered that the removal of the thermally labile components from the biobased feedstock increases the thermal stability making these materials very beneficial to subsequent melt processing of the material with a polymer matrix.

Biobased feedstocks are generally the co-products of renewable fuel processes. They are typically derived from grain-based agricultural materials that are used in wet or dry milling ethanol production facilities. Non-limiting examples of biobased materials used in fermentation processes in an ethanol production facility include one or more grain crops such as corn, wheat, rye, barley, milo, sorghum, and the like. In certain embodiments, the biobased feedstock is the thin stillage from an ethanol, butanol or distilled spirits production facility. In other embodiments, the biobased feedstock is the evaporated product of thin stillage, also known by those of ordinary skill in the art as condensed distillers solubles and if dried to moisture levels at or below 15% they are generally known as dried distillers solubles. In some embodiments, dried distillers solubles are well suited for use as an additive in a polymer matrix. A process for making dried distillers solubles from thin stillage is disclosed in U.S. Pat. Publication No. 2013/0206034, herein incorporated by reference in its entirety.

In one embodiment, the biobased feedstock includes a distillers soluble stream generated from a wet or dry mill ethanol, butanol or distilled spirits facility processing a grain crop or any mixture of grain crops. For example, the distillers solubles stream may comprise: (a) material of which more than 25% of the total solids is soluble in water at a pH value of 3 to 4 and in some embodiments more than 50% of the total solids is soluble in water within the noted pH value range, and/or (b) an acid detergent fiber content less than 13%, 10%, 5%, 2% or 1% on a dry matter weight percentage basis. As will be appreciated by those skilled in the art, determination of the acid detergent fiber (ADF) content is in accordance with the ANKOM Tech. Method. The ANKOM Tech. Method analysis follows FD PROC 39, which is based on AOCS Ba 6a-05. In this method, a test sample is sealed in a small bag and the bag immersed in acetyl trimethyl ammonium bromide/sulfuric acid solution that dissolves certain materials such as, for example, hemicelluloses and cell wall proteins leaving behind celluloses, lignins, cutins, some pectins, and the like. The bag is then washed, dried and re-weighed. The loss in weight is reported as acid detergent fiber.

Those of ordinary skill in the art recognize that conventional techniques in ethanol, butanol or distilled spirits processing may alter or modify the composition of the soluble stream. For purposes of this disclosure, such modifications are within the scope of this disclosure and the resulting soluble stream may be subjected to the method contemplated herein. For example, it is known in the art to utilize front-end and back-end fractionation practices that may alter a distillers solubles stream. Front-end fractionation is where a portion of the grain is removed prior to fermentation. Such portions removed may include fiber, protein, germ, and/or oil. Back-end fractionation can include known processing techniques such as oil recovery, fiber removal, protein concentration, protein isolate shifting such as washing protein from wet cake into distillers solubles to further enrich the distillers solubles with additional protein or materials. Additionally, filtration technology can also be used with various types of membrane processing. Furthermore, biobased feedstocks can be supplemented with other fermentable and non-fermentable products such as but not limited to sugars, starches, and food products that may impact the composition of the distillers solubles stream. In certain embodiments, the fermentation product shall be at least 25%, 50%, 75%, 90%, 95% and up to 100% agricultural grain or grains.

In one embodiment, the biobased feedstock may initially be extruded to form an extrudate. Any extruder suitable for the melt processing of thermoplastic polymers may be utilized to create the extrudate. Single screw and twin screw extruders are all capable of creating an extrudate comprising a biobased polymer. In some embodiments, the extrudate is formed in an extruder where at least some of the extruder zones are at temperatures above 130° C., above 140° C., above 150° C., above 160° C., above 180° C., above 220° C., or above 240° C. The extruder screw speed in various embodiments may be between 5 and 1000 rpm or between 20 and 500 rpm. The extrudate may be cooled and pelletized using conventional pelletization equipment and practices. Those of ordinary skill in the art with knowledge of this disclosure are capable of processing biobased feedstocks to form an extrudate in forms suitable to enable further separation of thermally labile components.

In another embodiment, thermoplastic polymer may be extruded with the biobased feedstock. A thermoplastic polymer may function as a binder for the extrudate, as a processing agent to assist in the extrusion of the biobased feedstock, or both. In certain embodiments, the biobased feedstock is included in the extrudable compositions with the thermoplastic polymer in amounts of typically 0.1% to 95% by weight. Non-limiting examples of thermoplastic polymers comprise polyamides, polyimides, polyurethanes, polyolefins, polystyrenes, polyesters, polycarbonates, polyketones, polyureas, polyvinyl resins, polyacrylates, polymethylacrylates, or combinations thereof. Polyolefins are well suited for certain applications. Polymer matricies in this instance may include polyolefins. A process for forming a melt processable composition comprising a biobased feedstock and a polymer matrix is disclosed in U.S. patent application Ser. No. 14/460,831, filed Aug. 14, 2014, and herein incorporated by reference in its entirety.

The extrusion processing of the biobased feedstock may remove at least a portion of thermally labile components from the biobased feedstock prior to being subjected to the separation techniques detailed in this disclosure. In certain embodiments, the processing of the biobased feedstock at elevated temperatures can result in the pyrolytic modification of the biobased feedstock. The pyrolytic modification of the biobased feedstock may occur without adversely impacting the remaining components of the feedstock. Those of ordinary skill in the art will recognize that the time exposure and rapid heating convention will be dependent upon the particular biobased feedstock, the selected heating convention, and desired properties of the resulting material. The pyrolytic modification of a biobased feedstock is set forth in detail in International Application No. PCT/US15/43611 filed Aug. 4, 2015, herein incorporated by reference in its entirety. The mechanism for removal of thermally labile components, such a pyrolytic modification or separation, may be selected to impart desired end properties of the processed biobased feedstock. For example, aesthetics, such as color may be impacted by the specific method selected to remove at least a portion of the thermally labile components.

The resulting extrudate, containing at least a portion of thermally labile components, is generally in a solid form, such as a pellet or granule, and subjected to separation methods to address further removal of at least a portion of the thermally labile components. Certain thermally labile components may also be susceptible to dissolution in a solvent. As such, solvent extraction may be employed in certain embodiments as the separation method. Non-limiting examples of solvent extraction methods include one or more of immersion, counter current washing, concurrent washing, or batch soaking of the extrudate. Additionally, various solvents can be used. Non-limiting examples of solvents comprise comprising at least one of water, ethanol, peroxide, sodium hypochlorite (bleach), iso-propanol, acetone, tetrahydrofuran, dimethylsulfoxide, dimethylforamide, diethyl ether, ethyl acetate and methyl ethyl ketone. Some embodiments involve heating the extrudate in solution to a temperature within a range of about 20° C. to about 120° C. The extrudate may be subsequently dried to remove excess solvent.

In certain embodiments, the processing of the extrudate into pellet or granular form may enable solvent extraction methods. For example, a water or solvent bath may be employed to cool the hot extrudate in strand form prior to pelletization. The water in the bath may function as a solvent and remove at least a portion of the thermally labile components in the extrudate. Similar applications involving underwater pelletizers are possible and may serve as to remove the thermally labile components.

The thermally labile components are removed from the biobased feedstock to impart thermal stability in the finished material. This renders the treated biobased feedstock useful as an additive in melt processing applications with a polymer matrix. Additionally, light weight additives may be desirable in certain composites. As a result of the solvent extraction, the treated biobased feedstock has a specific gravity lower than the untreated biobased feedstock. In some embodiments, the specific gravity of the treated biobased feedstock is at least 5%, or at least 10% lower than the untreated biobased feedstock.

Thermally labile components are organic compounds or polymers that generally outgas and/or decompose at temperatures below conventional polymer melt processing temps. In some embodiments, the thermally labile components outgas and/or decompose at temperatures above 120° C. It has been discovered to be very desirable to remove at least a portion of such compounds in order to minimize defects that can be attributed to the thermally labile components during melt processing with a polymer matrix. For example, the presence of and decomposition and/or outgassing of these thermally labile components may negatively impact the melt or the finished product due to such phenomenon as off-gassing, discoloration, and melt defects.

For purposes of this disclosure, thermal stability indicates a materials ability to withstand conventional melt processing temperatures and conventional processing rates without a significant loss of mass due to thermal degradation. A loss of mass due to thermal degradation during melt processing may adversely affect either the process or the resulting physical and aesthetic properties of the finished composite may be considered significant by those of ordinary skill in the art.

In another embodiment, a thermogravimetric analysis (TGA) may be utilized as an indication of the presence of thermal stability in the treated biobased feedstock. The TGA establishes a degradation onset temperature for a specific sample of treated biobased feedstock. The treated biobased feedstock has a degradation onset temperature greater than a non-treated biobased feedstock from which the treated biobased feedstock was formed. For certain embodiments, it is desirable to have the degradation onset temperature greater than a selected melt processing temperature with less than five percent mass loss, not including losses related to moisture. In one embodiment, it is desirable to have less than one percent mass loss at the selected melt processing temperature not including losses related to moisture. Yet in another embodiment, the degradation onset temperature of the treated biobased feedstock is greater than 175° C. One method for determining thermal stability utilizing TGA involves heating the sample of material at a relatively slow rate (i.e., 10° C./min) from room temperature to temperatures where all of the organic material within the sample decomposes (e.g., 300° C.).

FIG. 1 depicts a graph of two samples of a biobased feedstock that were subjected to thermogravimetric analysis to determine the degradation onset temperature. Sample A was not subjected to the solvent extraction of this disclosure. Sample B is the same biobased feedstock of Sample A but subjected to solvent extraction to remove some of its thermally labile components. The degradation onset temperature is the point of inflection following the loss of moisture on the TGA curve. The moisture loss on sample A and sample B generally occurs between 25° C. and 125° C. With regard to Sample A, the losses are about 10% when it reaches a degradation onset temperature of about 150° C. Sample B has a moisture loss of about 5% when it reaches a degradation onset temperature of about 250° C. The graphs of the TGA's are useful to determine the relative thermal stability of the materials.

In some embodiments, the pyrolyzed biobased feedstock of this disclosure is thermally stable at temperatures up to 350° C., 300° C., 280° C., 260° C., 240° C., 220° C., 200° C., or 180° C. with less than five percent loss of mass, not including moisture, as measured under the above noted TGA analysis at heating rate of 10° C./min. In other embodiments, the pyrolyzed biobased feedstock of this disclosure is thermally stable at temperatures up to 350° C., 300° C., 280° C., 260° C., 240° C., 220° C., 200° C., or 180° C. with less than two percent loss of mass, not including moisture, using TGA test parameters at heating rate of 10° C./min.

One particular enhancement resulting from the process for treating biobased feedstocks is the reduction of odor from the material. Biobased feedstocks generally have a very noticeable, and often undesirable odor. This may carry over through melt processing conditions and negatively impact the finished polymer. Various embodiments of treated biobased feedstocks produced in accordance with this disclosure have a more favorable odor rating, or rather a lack of noticeable odor in comparison to biobased feedstocks that have not been treated.

An additional feature of the treated biobased feedstock is the color. The treated biobased feedstock may have a lighter color than that of the biobased feedstock. More importantly, the resulting finished article produced in the end use application with the treated biobased feedstock often has a lighter color than it would have been with an untreated biobased feedstock and/or a lighter color than articles produced using pyrolysis methods to remove thermally labile components such as those described in International Application No. PCT/US15/43611. The lighter color may be desirable in certain end use applications. The treated biobased feedstock has an L* color value according to CIELAB color scale coordinates greater than the L* value of the untreated biobased feedstock and/or the pyrolysis treated biobased feedstock, as described in the referenced patent application. The CIELAB color scale coordinate shift indicates an overall lightening of the material.

The treated biobased feedstock exhibits a reduction of thermally labile components over an untreated biobased feedstock. Non-limiting examples of thermally labile components include hemicellulose and carbohydrates. Certain embodiments have less than 10 wt % thermally labile components remaining after solvent extraction. Other embodiments may have less than 5%, or less than 2%, thermally labile components remaining after separation of the components by solvent extraction.

The solvent extraction process of this disclosure may result in additional products beyond the treated biobased feedstock. The solvent extraction of thermally labile components from a biobased material results in an extractant stream containing compounds that, upon recovery from the stream, may be useful in other applications or suitable for further processing. The recovery of such materials from the extractant stream may enhance the overall economics of the separation of thermally labile components from the biobased feedstock. Non-limiting examples of components recoverable from the extractant stream comprise salts, sugars, and carbohydrates. Those of ordinary skill in the art will recognize that numerous methods may be utilized to address the recovery of the desired components from the extractant stream. For example, recovering methods may comprise known methods of centrifugation, particulate filtration, membrane filtration, distillation, hydrothermal carbonization and combinations thereof. Hydrothermal carbonization (HTC) is a process that through the use of heating of an aqueous solution to temperatures generally between 170° C. and 250° C., produce a char, which can be used as an energy source such as green-coal or as an additive within bioplastic formulations, and a filtrate which can be used directly, further refined and/or concentrated to produce a more valuable co-product, such as fertilizer. An exemplary method to process fermentation residue by way of hydrothermal carbonization is disclosed in U.S. Pat. Publication No. 2014/0033777, herein incorporated by reference in its entirety.

In certain circumstances it may be advantageous to condition the extractant stream prior to initiating any component recovery method. Non-limiting examples of conditioning step or steps comprise crystallization, pH adjustment to create a separable precipitate or use of pH adjustment to liquefy or make soluble an otherwise insoluble material within the solution to further improve extraction and separation capabilities. Enzyme and solvent addition or combinations thereof are two additional non-limiting examples of conditioning steps that can further enhance separation and extraction opportunities. In some embodiments, recovery of certain components from the extractant stream is more efficiently addressed if the stream is first subjected to an evaporative method to concentrate the components. Suitable evaporative methods are known to those of ordinary skill in the art and include methods such as drying.

The extractant stream, or any components separated from the stream, can be returned to an alcohol production facility for further use or processing. Such facilities include fermentation facilities for the production of ethanol or butanol where the extractant stream, or its components, can be further utilized. For example, the extractant stream or its components, may be subjected to enzymatic treatment, fermentation, distillation, concentration, drying, hydrothermal carbonization or any combination thereof.

The treated biobased feedstock is in a physical form well suited to serve as an additive for melt processing applications. The material may be in either granular or powder form with various particle sizes. The sizing of the particulates or powder may be selected to achieve the desired mixing with other components and thereby prevent segregation or other material handling issues. The mean particle size of the treated biobased feedstock may be less than 1000 microns, 500 microns, or even less than 150 microns. In one embodiment, the treated biobased feedstock is milled to a finer particle size, such as for example, less than 500 microns, less than 300 microns, less than 100 microns, less than 50 microns, less than 25 microns, or less than 10 microns. Non-limiting examples of milling equipment useful for this purpose include ball mills, jet mills and hammer mills. Those of ordinary skill in the art are capable of designating the specific sizing needed to address handling and mixing of the treated biobased feedstock.

The enhanced thermal stability, reduced odor, desired color and other beneficial properties of the treated biobased feedstock permit the use and application of the materials as additives in polymer composites formed through melt processing applications. Those of ordinary skill in the art are capable of combining the treated biobased feedstock with various polymer matrices and other optional additives to achieve desired properties for a composite material. The treated biobased feedstock may be included in final composite formulations in amounts of about 0.1-95% by weight, 0.1-75% by weight, 0.1-50% by weight, 0.1-25% by weight, 0.1-15% by weight and 0.1-10% by weight.

The polymer matrix functions as the host polymer and is a component of the melt processable composition. A wide variety of polymers conventionally recognized in the art as suitable for melt processing are useful as the polymeric matrix. They include both hydrocarbon and non-hydrocarbon polymers. Examples of useful polymeric matrices include, but are not limited to, polyamides, polyimides, polyurethanes, polyolefins, polystyrenes, polyesters, polycarbonates, polyketones, polyureas, polyvinyl resins, polyacrylates and polymethylacrylates or combinations thereof.

The polymer matrix is included in the melt processable compositions in amounts of typically greater than about 75% by weight, 50% by weight, 40% by weight, or 30% by weight. Those skilled in the art recognize that the amount of polymeric matrix will vary depending upon, for example, the type of polymer, the amount of treated biobased feedstock, the selected optional additives, the processing equipment, processing conditions and the desired end product.

In another aspect, the melt processable composition may contain other additives or adjuvants. Examples of conventional additives or adjuvants include, but are not limited to, antioxidants, light stabilizers, fibers, mineral fillers, catalysts, blowing agents, foaming additives, antiblocking agents, cross-linking agents, heat stabilizers, light stabilizers, viscosity stabilizers, moisture stabilizers, odor stabilizers, antistatic agents, impact modifiers, biocides, flame retardants, plasticizers, tackifiers, chain extenders, emulsifiers, colorants, processing aids, lubricants, coupling agents, pigments or combinations thereof. Those skilled in the art of melt processing are capable of selecting appropriate amounts and types of additives to match with a specific polymer matrix in order to achieve desired physical properties of the finished composite. In an alternative embodiment, it may be desirable to add one or more of these additives or adjuvants to the biobased feedstock prior to the separation of thermally labile components by solvent extraction.

The melt processable compositions may be prepared by any of a variety of ways using melt processing techniques. For example, the treated biobased feedstock, any optional additives or adjuvants, and the polymer matrix can be combined together by any of the blending means usually employed in the plastics industry, such as with a compounding mill, a Banbury mixer, or a mixing extruder. The materials may be used in the form, for example, of a powder, a pellet, or a granular product. The mixing operation is most conveniently carried out at a temperature above the melting point or softening point of the polymer. The resulting melt-blended mixture can be either extruded directly into the form of the final product shape or pelletized or otherwise comminuted into a desired particulate size or size distribution and fed to an extruder that melt-processes the blended mixture to form the final product shape. Alternatively, the composition may be molded into a desired form. The resulting composite exhibits superior performance results when produced using this protocol.

Melt-processing typically is performed at a temperature from 120° C. to 350° C., and more typically between 150° C. and 250° C., although optimum operating temperatures are selected depending upon the melting point, viscosity, or thermal stability of the composition. Different types of melt processing equipment, such as extruders, may be used to process the melt processable compositions of this invention. In certain embodiments, twin screw extruders are well suited for melt mixing the components of the composite.

The resulting articles produced by melt processing the inventive composition exhibit superior mechanical characteristics in the field of composite structures. For example, a composite comprised of a treated biobased feedstock may exhibit an increase in one or more characteristic, such as flexural modulus, flexural strength, tensile strength, tensile modulus and impact strength over composites with untreated biobased feedstocks. In other embodiments, the incorporation of a treated biobased feedstock at relatively high loading levels in a polymer matrix results in a composite without dramatic or significant change in physical characteristics over the neat polymer. The higher loading levels in the polymer matrix without the significant loss of physical properties can enable substantial economic benefit.

The composites of this invention are suitable for manufacturing articles in the construction, consumer goods and automotive industries. For example, articles incorporating the composition of the present invention may include: molded architectural products, forms, films, sheet, automotive parts, building components, or household articles.

EXAMPLES

In Examples, 1-2, samples of dried distillers solubles ("DDS"), derived from a corn fermentation process for renewable fuel and produced in accordance with U.S. Pat. Publication No. 2013/0206034, were combined with thermoplastic polymers as noted in Table 1. In a first processing step, the DDS material was compounded with either linear low density polyethylene (Sclair 31E, commercially available from Nova Chemicals, Calgary, AB) or high density polyethylene (6719, commercially available from Exxon Chemical, Houston, Tex.). In Examples 1-2, DDS and thermoplastic polymer were compounded using a 36:1 L:D, co-rotating twin screw extruder commercially available from American Leistritz Corporation (Sommerville, N.J.). The materials were compounded at 300 rpm screw speed at 7 kg/hr output using a flat temperature profile, 180° C. for all zones was utilized for the compounding. Examples were extruded four strand die (0.125" diameter strands) onto a belt, pelletized and collected. Table 1 shows the formulations produced.

TABLE 1

Formulations for Examples 1 and 2.

| Example | Biobased Feedstock (wt %) | Exxon 6719 HDPE (wt %) | Sclair 31E LLDPE (wt %) |
|---|---|---|---|
| 1 | 85 | 15 | |
| 2 | 85 | | 15 |

The biobased composites were subsequently extracted with various aqueous solutions. In Table 2, Examples 3-6 were produced by treating the pellets of Examples 1 or 2 with either water or dilute hydrogen peroxide for 1 hour at 60° C.

TABLE 2

Extraction Conditions for Examples 3-6.

| Example | Example 1 | Example 2 | Extraction Conditions |
|---|---|---|---|
| CE1 | 100 | | None |
| CE2 | | 100 | None |
| 3 | 100 | | $H_2O$, 60° C., 1 hour |
| 4 | 100 | | $H_2O_2$, 60° C., 1 hour |
| 5 | | 100 | $H_2O$, 60° C., 1 hour |
| 6 | | 100 | $H_2O_2$, 60° C., 1 hour |

The thermal stability of the resulting materials was determined using a Mettler Toledo STAR 1 Thermogravimetric Analysis (TGA) unit (Mettler-Toledo LLC, Columbus, Ohio). All Examples, including comparative example CE1 were characterized using the same temperature ramp profile (room temperature to 300° C. ramp at 10° C./min). Biobased composite Examples 3-6 showed markedly improved thermal stability when compared to the Comparative Examples 1-2 when characterized using the degradation onset temperature determined through thermogravimetric analysis. Thermal stability and percent mass loss are summarized in Table 3.

TABLE 3

Degradation Onset Temperature and Mass Loss for Examples 3-6 and Comparative Examples CE1-CE2

| Example | Mass Loss (%) | Degradation Onset (° C.) |
|---|---|---|
| CE1 | 0 | 140 |
| CE2 | 0 | 140 |
| 3 | 22.2 | 225 |
| 4 | 25.2 | 255 |
| 5 | 32.5 | 225 |
| 6 | 33.2 | 255 |

As can be seen from Table 3, the thermal stabilities for all of the treated biobased feedstock in examples 3-6 were markedly improved relative to the control CE1 and CE2 as evidenced by the increase in the degradation onset temperature. Moreover, percent mass loss and degradation onset temperature generally increased as a function of increased temperature and exposure time.

For Examples CE1 and 3-6, the biobased composites were dry blended with high density polyethylene (5502, commercially available from Ineos, League City, Tex.), compounded in a using a 36:1 L:D, co-rotating twin screw extruder commercially available from American Leistritz Corporation (Sommerville, N.J.). The materials were compounded at 300 rpm screw speed at 7 kg/hr output using a flat temperature profile, 180° C. for all zones was utilized for the compounding. The samples were injection molded into ASTM test specimens using an Engel 85 ton injection molder fitted with and ASTM tool. All specimens were tested for flexural, tensile and impact properties following ASTM D790, D638 and D256; respectively. The formulations for each of the Examples screened are given in Table 4. Mechanical property data for these specimens is given in Table 5-6.

TABLE 4

Formulations for Comparative Examples CE3 and Examples 7-10

| Example | Comparative Example 1 (wt %) | Example 3 (wt %) | Example 4 (wt %) | Example 5 (wt %) | Example 6 (wt %) | Ineos 5502 HDPE (wt %) |
|---|---|---|---|---|---|---|
| CE3 | 20 | | | | | 80 |
| 7 | | 30 | | | | 70 |
| 8 | | | 30 | | | 70 |
| 9 | | | | 30 | | 70 |
| 10 | | | | | 30 | 70 |

TABLE 5

Mechanical Properties for Comparative Examples CE3 and Examples 7-10

| Example | Flexural Modulus (MPa) | Flexural Strength (MPa) | Impact Strength Notched Izod (J/m) | Impact Strength Unnotched Izod (J/m) |
|---|---|---|---|---|
| CE3 | 690 | 21 | 86 | 494 |
| 7 | 875 | 25 | 76 | 1005 |
| 8 | 875 | 25 | 74 | 891 |
| 9 | 950 | 27 | 67 | 1183 |
| 10 | 950 | 27 | 72 | 975 |

TABLE 6

Tensile and Elongation Results for CE3 and Examples 7-10

| Example | Tensile Modulus (MPa) | Tensile Strength (MPa) | Elongation at Break (%) |
|---|---|---|---|
| CE3 | 682 | 17 | 17.5 |
| 7 | 972 | 17 | 11.6 |
| 8 | 944 | 18 | 13.7 |
| 9 | 1083 | 19 | 10.9 |
| 10 | 1082 | 19 | 11.8 |

As can be seen from Tables 5 and 6, the mechanical properties for the Biobased Composites 7-10 from the extracted masterbatches show improved properties when compared to Comparative Example 3.

From the above disclosure of the general principles and the preceding detailed description, those skilled in this art will readily comprehend the various modifications to which the present method is susceptible. Therefore, the scope of the invention should be limited only by the following claims and equivalents thereof.

What is claimed is:

1. A method comprising extruding a biobased feedstock to form an extrudate, and separating a thermally labile component from the extrudate by solvent extraction to form a treated biobased feedstock.

2. The method according to claim 1, further comprising extruding at least one thermoplastic polymer with the biobased feedstock to form the extrudate.

3. The method according to claim 2, wherein the thermoplastic polymer is selected from the group consisting of polyamides, polyimides, polyurethanes, polyolefins, polystyrenes, polyesters, polycarbonates, polyketones, polyureas, polyvinyl resins, polyacrylates, polymethylacrylates, and combinations thereof.

4. The method according to claim 1, wherein solvent extraction comprises heating the extrudate in solution to a temperature within a range of about 20° C. to about 120° C.

5. The method according to claim 1, wherein separating comprises immersion, counter current washing, concurrent washing, or batch soaking of the extrudate.

6. The method according to claim 1, wherein the treated biobased feedstock is thermally stable in a subsequent melt processing step.

7. The method according to claim 1, further comprising drying the treated biobased feedstock to remove excess solvent.

8. The method according to claim 1, wherein solvent extraction includes solvents comprising at least one solvent selected from the group consisting of water, ethanol, peroxide, sodium hypochlorite, iso-propanol, acetone, tetrahydrofuran, dimethylsulfoxide, dimethylforamide, diethyl ether, ethyl acetate and methyl ethyl ketone.

9. The method according to claim 1, wherein the biobased feedstock is derived from at least one grain.

10. The method according to claim 9, wherein the grain is comprised of one or combinations of corn, wheat, rye, barley, milo, or sorghum.

11. The method according to claim 1, wherein the biobased feedstock comprises thin stillage condensed distillers solubles, or dried distillers solubles.

12. The method according to claim 1, wherein the biobased feedstock comprises at least one of (i) distillers solubles stream having water soluble solids greater than 25% of total solids at a pH of 3 to 4, or (ii) a distillers solubles stream having an acid detergent fiber value of less than 13%, and greater than 1% on a dry matter weight basis.

13. The method according to claim 1, wherein the treated biobased feedstock has a degradation onset temperature greater than a non-treated biobased feedstock from which the treated biobased feedstock was formed.

14. The method according to claim 1, wherein the treated biobased feedstock has a specific gravity lower than the untreated biobased feedstock.

15. The method according to claim 1, wherein the treated biobased feedstock has an L* color value according to CIELAB color scale coordinates greater than the L* value of the biobased feedstock.

16. The method according to claim 1, further comprising capturing an extractant stream and recovering one or more components from the extractant stream.

17. The method according to claim 16, wherein the recovering components comprises centrifugation, particulate filtration, membrane filtration, distillation and combinations thereof.

18. The method according to claim 17, further comprising conditioning the extractant prior to recovering components.

19. The method according to claim 18, wherein conditioning comprises crystallization, pH adjustment, enzymatic addition, solvent addition, or combinations thereof.

20. The method according to claim 16, wherein recovering one or more of components comprises concentrating the one or more components by evaporation.

21. The method according to claim 1, further comprising returning an extractant stream, or one or more components from the extractant stream to a fermentation-derived renewable fuels or distilled spirits production facility for processing.

22. The method according to claim 21, wherein the processing comprises enzymatic treatment, fermentation, distillation, concentration, drying, hydrothermal carbonization or any combination thereof.

23. The method according to claim 1, wherein extruding removes the thermally labile component from the biobased feedstock by pyrolytic modification.

24. The method of claim 1 further comprising the step of melt processing the treated biobased feedstock with a polymer matrix.

25. The method according to claim 24, wherein the polymer matrix is selected from the group consisting of polyamides, polyimides, polyurethanes, polyolefins, polystyrenes, polyesters, polycarbonates, polyketones, polyureas, polyvinyl resins, polyacrylates, polymethylacrylates, and combinations thereof.

26. The method according to claim 24, further comprising incorporating, prior to or during melt processing, additives and adjuvants, selected from the group consisting of antioxidants, light stabilizers, fibers, mineral fillers, catalysts, blowing agents, foaming additives, antiblocking agents, cross-linking agents, heat stabilizers, light stabilizers, viscosity stabilizers, moisture stabilizers, odor stabilizers, antistatic agents, impact modifiers, biocides, flame retardants, plasticizers, tackifiers, chain extenders, emulsifiers, colorants, processing aids, lubricants, coupling agents, pigments and combinations thereof.

27. The method according to claim 24, wherein the biobased feedstock is selected from the group consisting of thin stillage, condensed distillers solubles, dried distillers solubles and combinations thereof.

28. A process of forming an article, the process comprising: extruding an extrudate comprising a treated biobased feedstock material and polymer matrix to form the article, wherein the treated biobased feedstock has a degradation onset temperature greater than a biobased feedstock from which the treated biobased feedstock was formed.

29. The process of claim 28, further comprising adding an additive or adjuvant prior to or during the extruding, the additive or adjuvant selected from the group consisting of antioxidants, light stabilizers, fibers, mineral fillers, catalysts, blowing agents, foaming additives, antiblocking agents, cross-linking agents, heat stabilizers, light stabilizers, viscosity stabilizers, moisture stabilizers, odor stabilizers, antistatic agents, impact modifiers, biocides, flame retardants, plasticizers, tackifiers, chain extenders, emulsifiers, colorants, processing aids, lubricants, coupling agents, pigments and combinations thereof.

30. The process of claim 28, wherein the treated biobased feedstock material comprises a non-distillate product of a corn to ethanol fermentation process.

31. The process of claim 28, wherein the non-distillate product of the corn to ethanol fermentation process is dried distillers solubles having a moisture content of less than 15 percent by weight.

32. The process of claim 28, wherein the non-distillate product of the corn to ethanol fermentation process is condensed distillers solubles.

33. The process of claim 28, wherein the treated biobased feedstock material comprises distillers solubles having water soluble solids greater than 25% of total solids at a pH of 3 to 4, and an acid detergent fiber value of less than 10 percent and greater than 1% by weight.

34. The process of claim 28, wherein extruding the treated biobased feedstock and the at least one melt processable polymer is at a temperature greater than 170° C. to less than 350° C.

35. The process of claim 28, wherein the degradation onset temperature of the treated biobased feedstock is greater than 175° C.

36. The process of claim 28, wherein the treated biobased feedstock comprises 0.1 to 95 percent of the extrudate.

* * * * *